United States Patent
Mohammad

[19]

[11] Patent Number: 6,162,197
[45] Date of Patent: Dec. 19, 2000

[54] RETRACTABLE NEEDLE ASSEMBLY AND METHOD OF MAKING THE SAME

[76] Inventor: Owais Mohammad, 5004 Rittenhouse St., Riverdale, Md. 20737

[21] Appl. No.: 09/218,040

[22] Filed: Dec. 22, 1998

[51] Int. Cl.[7] .................................................. A61M 5/32
[52] U.S. Cl. ........................................ 604/195; 604/196
[58] Field of Search .................... 604/194, 195, 604/115, 181, 187, 190, 191, 192, 198, 110, 218, 197, 263, 200, 201, 204–206, 232, 244, 88, 82, 87

[56] References Cited

U.S. PATENT DOCUMENTS

| | | | |
|---|---|---|---|
| 3,134,380 | 5/1964 | Armao . | |
| 4,425,120 | 1/1984 | Sampson | 604/198 |
| 4,664,654 | 5/1987 | Strauss | 604/198 |
| 4,900,311 | 2/1990 | Stern | 604/198 |
| 4,923,445 | 5/1990 | Ryan | 604/195 |
| 4,998,924 | 3/1991 | Ranford | 604/798 |
| 5,011,475 | 4/1991 | Olson | 604/192 |
| 5,086,780 | 2/1992 | Schmitt | 604/194 |
| 5,106,379 | 4/1992 | Leap | 604/198 |
| 5,125,414 | 6/1992 | Dysarz | 128/763 |
| 5,232,456 | 8/1993 | Gonzalez | 604/192 |
| 5,246,428 | 9/1993 | Falknor | 604/198 |
| 5,279,579 | 1/1994 | D'Amico | 604/192 |
| 5,290,255 | 3/1994 | Vallelunga | 604/197 |
| 5,423,758 | 6/1995 | Shaw | 604/195 |
| 5,573,513 | 11/1996 | Wozencroft | 604/198 |
| 5,591,138 | 1/1997 | Vaillancourt | 604/263 |
| 5,695,475 | 12/1997 | Best, Jr. et al. | 604/198 |
| 5,769,826 | 6/1998 | Johnson et al. | 604/195 |
| 5,788,677 | 8/1998 | Botich et al. | 604/195 |

Primary Examiner—Wynn Wood Coggins
Assistant Examiner—Manuel Mendez
Attorney, Agent, or Firm—Papan Devnani, Esq.; C. C. Shroff

[57] ABSTRACT

A retractable syringe needle, including a needle assembly featuring a needle-holding mechanism containing a hub and a means for securing a syringe barrel to the hub, a hypodermic needle extending through the hub; and a pin connected with said hub. The needle assembly is positioned inside a tubular container which has a tubular wall with a first longitudinal slot therein. The container has a first end adapted to receive a syringe barrel, and a second open end adapted to receive a syringe needle. The needle assembly is slidably mounted in the container so that the first longitudinal slot slidably engages the pin. The needle assembly may be moved from a first position where the needle is within the container to a second position where the needle is exposed by sliding the pin toward the second open end of the container and causing the needle to pass through the second open end. The retractable syringe needle additionally features a means for biasing the needle assembly toward said first position; and a means for releasably engaging the pin at a defined location in said first longitudinal slot so as to hold said needle assembly in the position which exposes the needle. Similar retractable needles for use in administration of intravenous fluids or collection of blood samples are also disclosed.

33 Claims, 14 Drawing Sheets

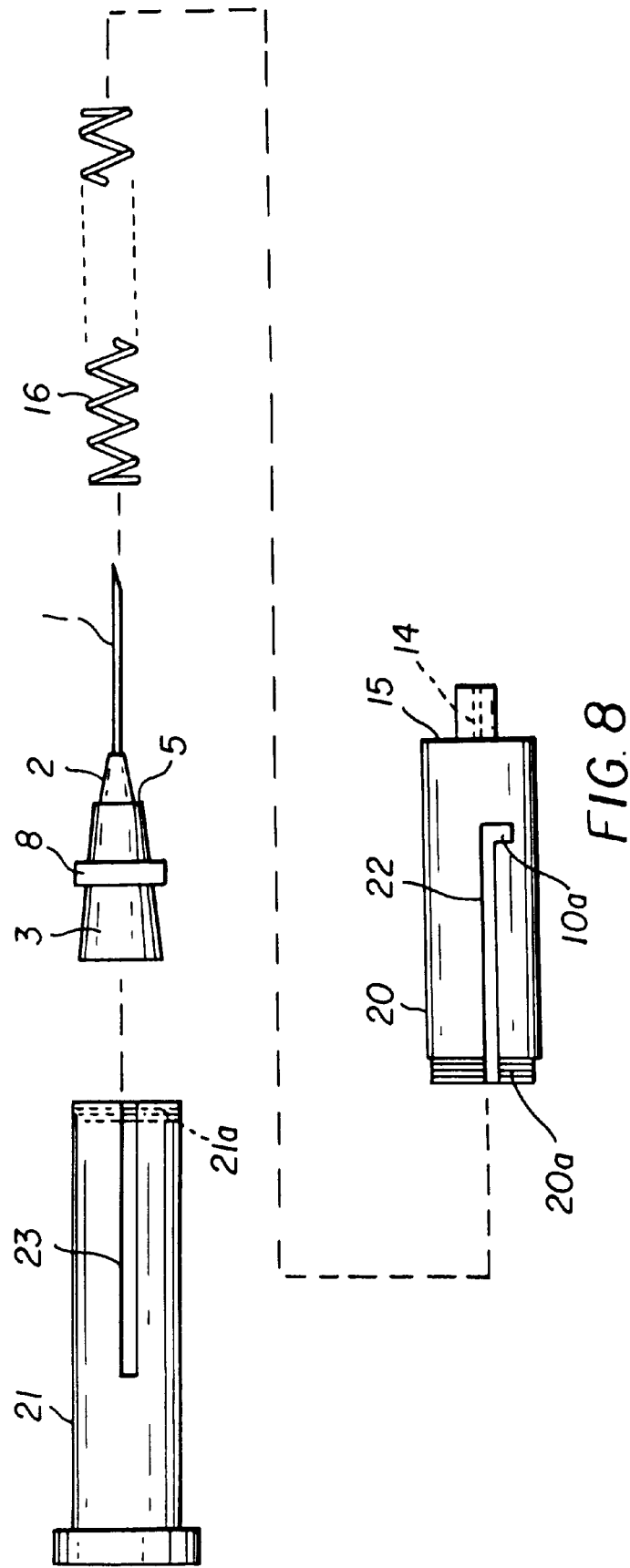

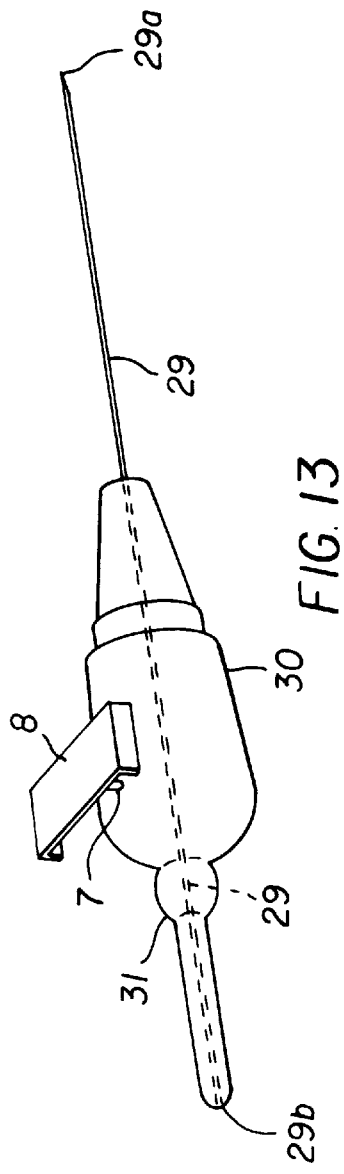
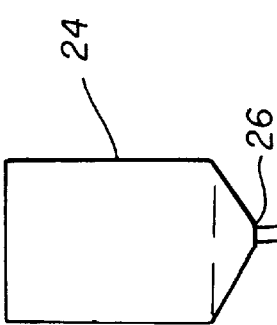
FIG. 13
FIG. 12

RETRACTABLE NEEDLE ASSEMBLY AND METHOD OF MAKING THE SAME

BACKGROUND OF THE INVENTION

The present invention generally refers to hypodermic syringe needles for medical use. More particularly, the invention relates to hypodermic safety needles which retract into a container when not in use, preventing unintentional contact with the needle.

Prior art injection needles feature hollow needles which extend through a plastic hub. To prevent a user from accidentally pricking himself with the point of a needle, the needle is covered with a removable cover. Such covers frictionally engage the plastic hub, and may be readily removed once the needle is attached to a syringe barrel. After use, the cover may be reattached to the needle assembly, which is then separated from the syringe barrel and discarded. However, there is an unacceptable risk of accidental injury resulting from contact with the point of the needle during the recapping step. This is particularly dangerous as biological fluids contaminating the needle could enter the user's bloodstream. An improved means of covering a used injection needle is needed.

A wide variety of needles having a means for shielding a syringe needle from accidental contact with a user's fingers have been developed. For example, U.S. Pat. No. 4,900,311, issued to Stem on Feb. 13, 1990, discloses a hypodermic syringe having a syringe barrel, an injection needle attached to the syringe barrel, and a needle guard of elliptical cross section disposed around the syringe barrel The needle guard may be moved from a first position which covers the needle to a second position which exposes the needle. When the guard is in the second position, tabs on the interior of the guard engage slots on the syringe barrel, locking the guard into position. When the tabs are released from the slots by squeezing the elliptical guard along its longitudinal axis, a spring causes the guard to move into the first position, hiding the needle. The entire syringe assembly is then discarded.

This device, while useful, does have certain drawbacks. The syringe barrel used with this assembly has a highly specialized structure; a generic syringe barrel cannot readily be substituted. Also, the syringe barrel cannot readily be sterilized and reused. No provision for separation of the needle from the syringe barrel without removing the syringe needle from the protective needle guard is provided. Finally, there is the risk of accidentally squeezing the elliptical needle guard, causing the spring to move the needle guard into a position which conceals the needle prior to use of the needle.

U.S. Pat. No. 4,664,654, issued to Strauss on May 12, 1987, discloses a two piece needle shield comprising a sliding member and a stationary member. A latch holds the sliding member in position. When the latch is released, a spring causes the sliding member to retract inside the stationary member exposing the needle. However, this device causes the user to place his hand in proximity to the needle at the time it is exposed, increasing the likelihood of injury from accidental contact with the needle.

U.S. Pat. No. 5,246,428, issued it Falknor on Sep. 21, 1993, discloses a needle safety mechanism comprising a base adapted to be fixed with respect to the needle, and a sheath ,which is movable between a first position which exposes the needle and a second position which covers the needle. A latch cooperative between the base and the sheath may be used to releasably latch the sheath in the position which covers the needle. A spring biases the sheath into the needle covering position. No mechanism for latching the sheath in a position which exposes the needle is provided, however. This may be an inconvenience for workers who wish to see the precise spot where they are administering an injection.

U.S. Pat. No. 5,279,579, issued to D'Amico on Jan. 18, 1994, discloses a self-capping injection needle assembly which includes a hub slidably positioned within a cylindrical cover adapted to receive a syringe barrel, and a needle mounted on the hub. A spring biases the hub into a position in which the needle is contained within the tubular cover. When the spring is compressed, the hub may slide into a position which exposes the needle. The hub includes a pin which slidably engages a longitudinal groove in the tubular cover. The groove includes a transverse leg adapted to receive the pin. When the pin is positioned in the transverse leg, the hub is releasably locked into a position which exposes the needle. The hub has a threaded female joint which may be screwed onto a syringe barrel having a corresponded threaded male joint. Different size tubular covers may be used for different size syringe barrels.

This device has certain disadvantages. First, in a medical environment time is often a critical factor. A more rapid method of affixing a needle to a syringe barrel than screwing it on is desirable. Also, only syringe barrels with a specific type of joint adapted to mate with the hub are usable with this device. Most commonly used medical syringe barrels have frusto-conical tips which frictionally engage syringe needle hubs having, frusto-conical cavities therein; such commonly used barrels cannot be used with the threaded connections envisioned by D'Amico. D'Amico requires that a hub having a specific diameter must be used with a tubular cover having an inner diameter which is substantially equal to the hub diameter. Most commonly available syringe needle hubs have a single standard size, and cannot be used with a range of tubular cover sizes. Therefore, D'Amico's invention necessitates creation of a range of expensive and specialized syringe needles having a range of hub sizes. Also, since the diameter of D'Amico's hub is very nearly equal to the interior diameter of the tubular cover, it is difficult to insert a hub having a protruding pin into the cover. An easy method of assembling such a device is desirable.

There is a long-felt need in the art for a safety needle assembly having a retractable needle which may be easily assembled and cost effective and which may be used with commonly available syringe barrels having frusto-conical tips which frictionally engage a syringe needle assembly. The required safety needle assembly must also avoid the other disadvantages of known prior art devices. It is an object of this invention to provide such a safety needle assembly.

SUMMARY OF THE INVENTION

The present invention provides a disposable hypodermic syringe needle which retracts into a container for safe disposal. The container features a tubular wall having a longitudinal slit therethrough. One end of the container is open so that a syringe barrel may be received therein. The second end of the container has an opening which is sufficiently large to receive a hypodermic needle, but too small to receive a syringe barrel. A hypodermic needle assembly is contained within the container. This assembly features a hypodermic needle which is affixed to a hub. An annular sleeve defining a frusto-conical cavity surrounds the periphery of the hub. The cavity in the annular sleeve is designed to frictionally engage a frusto-conical tip of a syringe barrel. A spring engages the hub of the needle assembly and a ridge on the interior of the wall of the second end of the container. This spring biases the hub away from the second end of the container so that the needle attached to the hub is hidden within the container. When the spring is compressed, the needle is able to pass through the opening of the second end of the container. A pin attached to the annular sleeve is slidably engaged by the longitudinal slit in the container wall, holding the needle within the container while allowing it to slide back and forth. A knob mounted on the pin is positioned outside the container. The knob is too large to pass through the longitudinal slit, and acts to position the hub of the needle along the axis of the container. The knob holds the needle assembly in the container. In the absence of the knob the needle assembly would fall in the lower level of the container and finally fall out of the container. When the knob is pushed toward the second end of the container, the hub moves toward the second end of the container, compressing the spring and causing the needle to emerge through the second open end of the container. A means for reversibly engaging the knob when the spring is compressed is also provided. This allows the needle to be retained in an exposed position.

The needle may be frictionally secured to a syringe barrel having a plunger slidably mounted therein. More specifically, a syringe barrel having a frusto-conical tip is secured to the needle assembly by inserting the frusto-conical tip of the syringe barrel into the cavity of the annular sleeve until the barrel tip is frictionally secured to the barrel sleeve.

Additional features of the invention will be described in the detailed description of the preferred embodiments. Any syringe barrel having an appropriately shaped frustoconical tip may be used with the inventive needle assembly having standard frustoconical hub.

Other embodiments of this invention are contemplated. The needle assembly of this invention may be attached to an IV tube and used for intravenous administration of fluids. Also, a modified needle assembly having a double-ended hypodermic needle which is affixed to a hub may be used to withdraw samples of venous blood.

DESCRIPTION OF THE DRAWINGS

FIGS. 1, 1*a*, and 1*b* illustrate a hypodermic needle for use in the syringe assembly of this invention.

FIG. 8 is an exploded view of the retractable hypodermic safety needle within a container shown in FIG. 3.

FIG. 12 shows an apparatus for administering a fluid intravenously.

FIG. 13 shows a modified version of the needle assembly of FIG. 1, for use in taking blood samples in the tubes.

DETAILED DESCRIPTION

Figure 1:
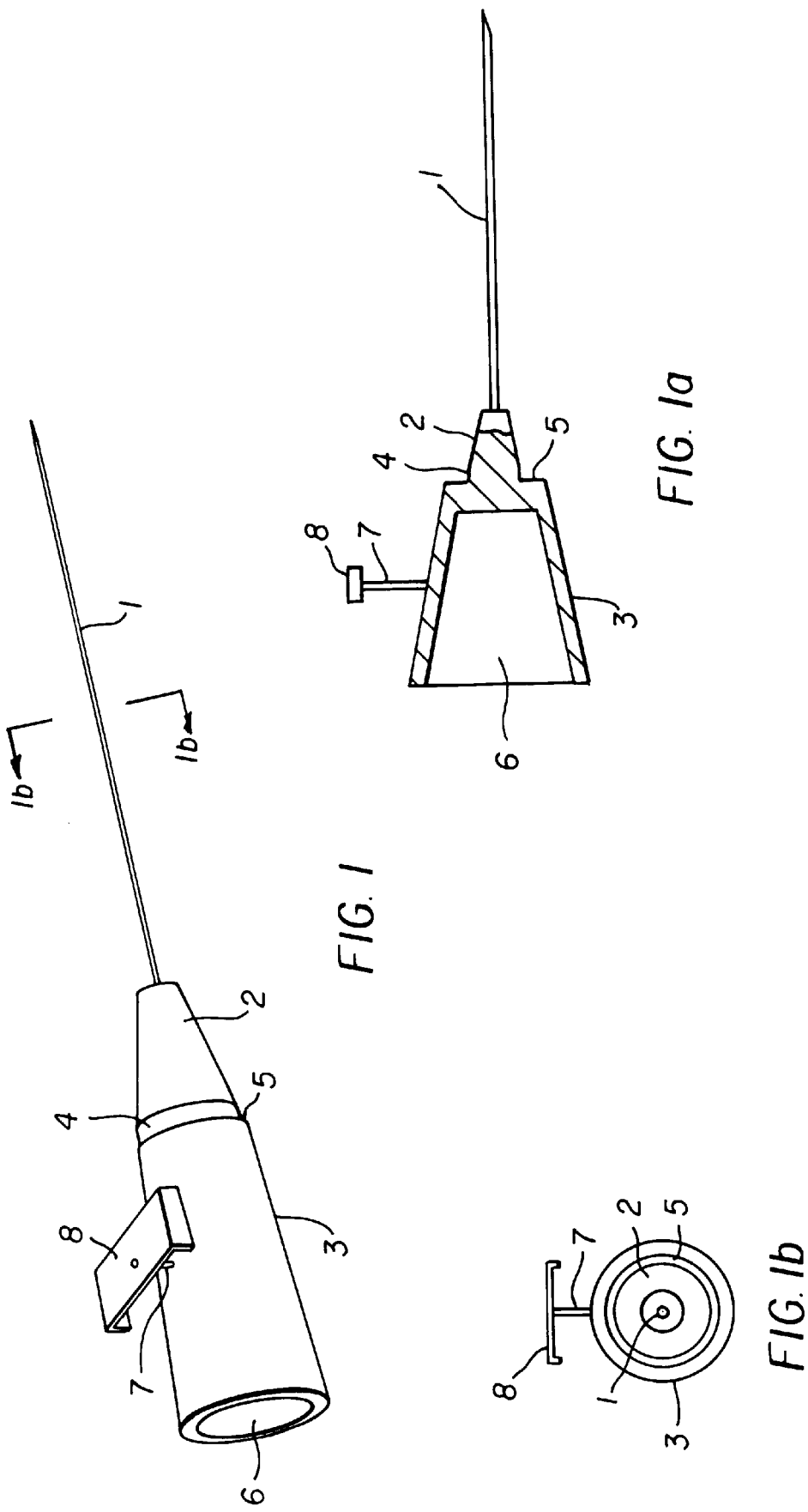

FIG. 1 illustrates a hypodermic needle for use in the syringe assembly of this invention. Needle 1 is affixed to hub 2. A hollow bore runs longitudinally through needle 1 and hub 2. An annular sleeve 3 is affixed to the outer periphery 4 of hub 2. A ledge 5 encircling hub 2 is defined by the edge of sleeve 3. Sleeve 3 defines a frusto-conical cavity 6 adapted to frictionally engage a frusto-conical tip of a syringe barrel, as shown in the cross-sectional view of FIG. 1*a*. A pin 7 is affixed to the outer surface of sleeve 3. A knob or crosspiece 8 is mounted on pin 7. Crosspiece 8 should be positioned so that, when viewed along the axis of needle 1, piece 8 and pin 7 intersect at a right angle (FIG. 1*b*). Although pin 7 and crosspiece 8 may be manufactured separately and secured together, it is preferred that 7 and 8 be manufactured as a single piece.

Figure 2:
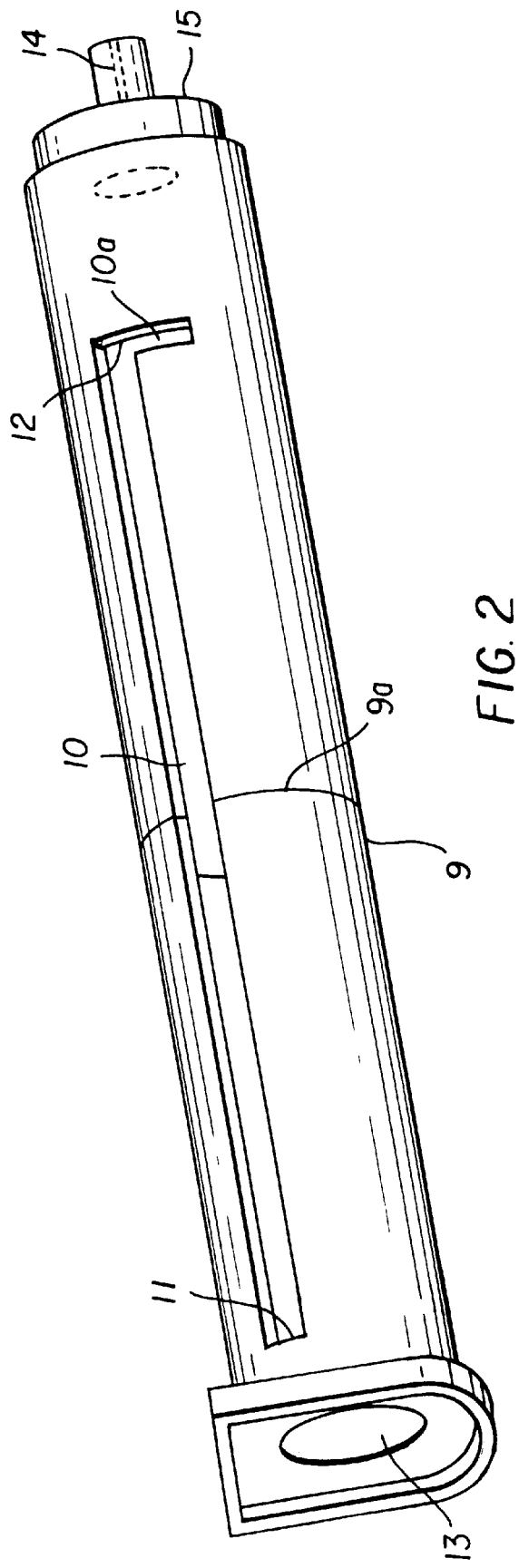
FIG. 2 shows a grooved container designed to contain the needle of FIG. 1.

FIG. 2 shows a grooved container designed to contain the needle of FIG. 1. The container has a tubular wall 9 having a longitudinal slit 10 therethrough. A first end of the container has an opening 13 adapted to receive a syringe barrel. The second end of the container has an opening 14 which is large enough to allow needle 1 to pass therethrough, but too small to admit a syringe barrel or a human finger. A ledge 15 on the second end of the container runs from the interior of wall 9 to the edge of opening 14. Slit 10 runs from a point near the first end of the container, without reaching the first end of the container, to a point near the second end of the container, without reaching the second end of the container. A second slit 10*a*, running a part of the way around the circumference of wall 9, intersects slit 10 near the second end of the container.

Figure 3:
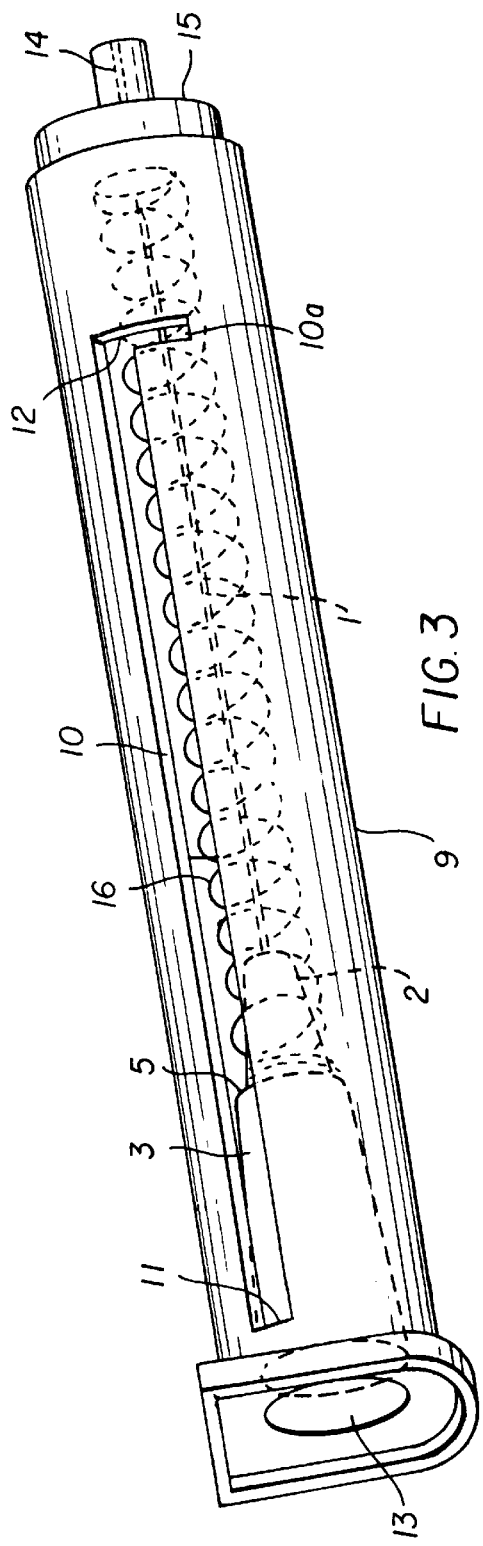
FIGS. 3 and 3*a* show a retractable hypodermic safety needle within a container, with the needle in a retracted configuration.
Figure 3A:
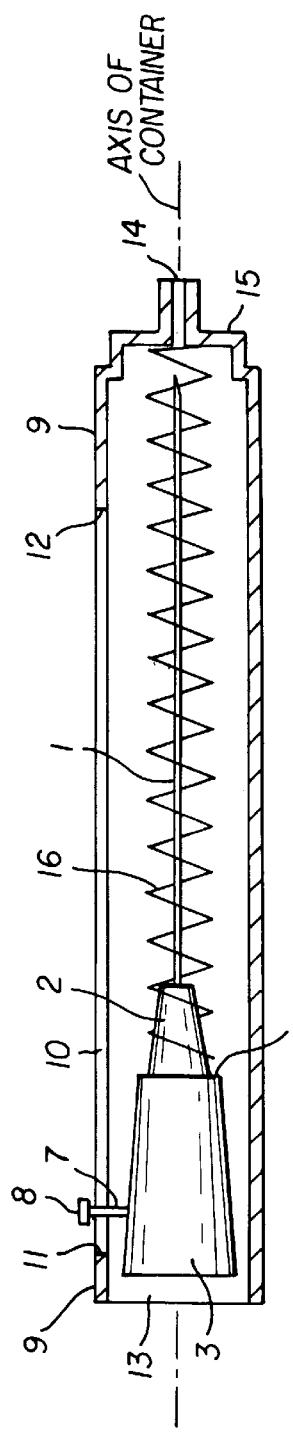

FIG. 3 shows how the needle assembly of FIG. 1 is contained within the container of FIG. 2. The needle assembly is positioned within the container with pin 7 slidably engaging slit 10. Crosspiece 8 helps to retain pin 7 within slit 10. Piece 8 is sufficiently large that it cannot pass through slit 10 into the interior of the container, and is rigidly secured to a defined position along the length of pin 7, where the defined position on pin 7 is chosen so that hub 2 of the needle assembly is positioned along the cylindrical axis of the container, as shown in the cross-sectional view of FIG. 3*a*. More particularly, the distance between the axis of hypodermic needle 1 and crosspiece 8 is equal to the one half the external diameter of the wall 9 of the container. This retains needle 1 along the axis of the container. Removal of knob 8 would allow pin 7 to slip out of slot 10, causing hub 2 to fall against the side of wall 9 and ultimately fall out of the holder via end 13.

A needle having a hub of any desired size may be used in a container having any desired radius without losing the desired axial orientation of needle 1 by simply changing the distance between the axis of needle 1 and crosspiece 8. This makes it unnecessary to manufacture a wide variety of needle hubs, with each needle hub being reserved for a different container size, as required by D'Amico.

A spring 16 is also positioned within the container. A first end of spring 16 engages ledge 15 at the second end of container 1, while the second end of spring 16 engages ledge 5 encircling hub 2. The spring acts to bias hub 2 away from the second end of the container so that needle 1 is effectively concealed within the container. This allows the user to effectively handle the assembly without pricking his fingers.

Figure 4:
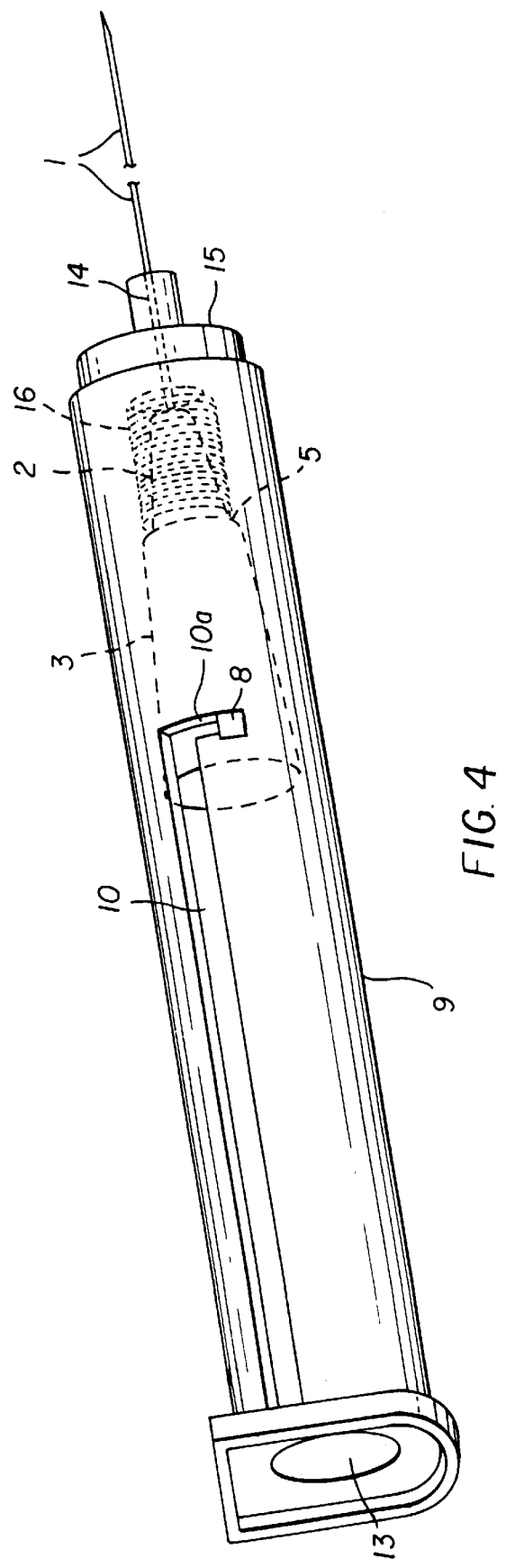
FIG. 4 shows a retractable hypodermic safety needle within a container, with the needle in an exposed configuration.

When one is ready to use the needle, needle 1 may be exposed by pushing hub 2 toward the second end of the container. This is most easily done by manually sliding crosspiece 8, attached to pin 7, along slot 10 with the user's thumb or finger. As hub 2 approaches the second end of the container, spring 16 is compressed and needle 3 passes through opening 14 in the container and is exposed. Since needle 1 is directed along the axis of the container, it is very easy to direct the needle through opening 14. When pin 7 reaches end 12 of slot 10, the needle is rotated by pushing pin 7 into slot 10a. Slot 10a acts as a stop, preventing spring 16 from decompressing and causing needle 1 to retract into the container. An illustration of the needle assembly in this configuration is shown in FIG. 4. This has the great advantage that one may expose a sheathed needle without having to position one's fingers near the needle itself, as is done when exposing the sheathed needle described by Strauss (vide supra).

Figure 9A:
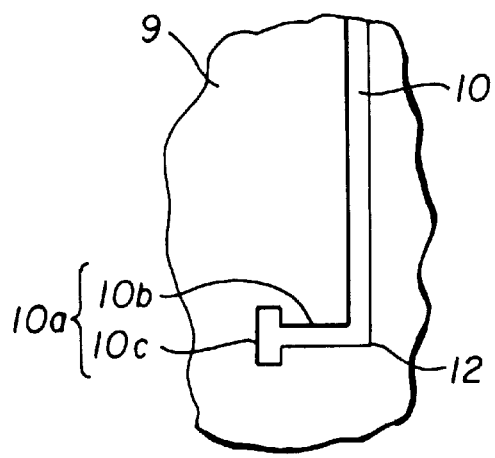
FIGS. 9*a* through 9*c* show various embodiments of locking mechanisms to hold a retractable needle in an exposed configuration.
Figure 9B:
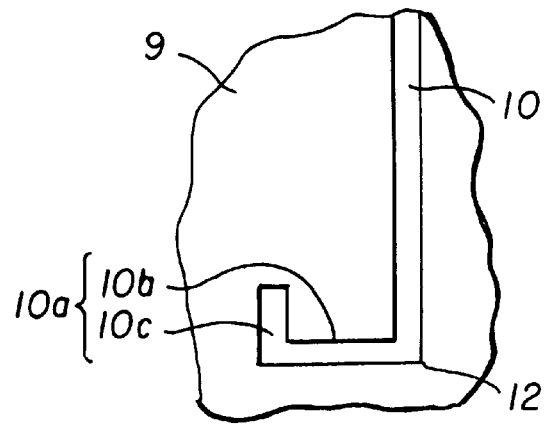
Figure 9C:
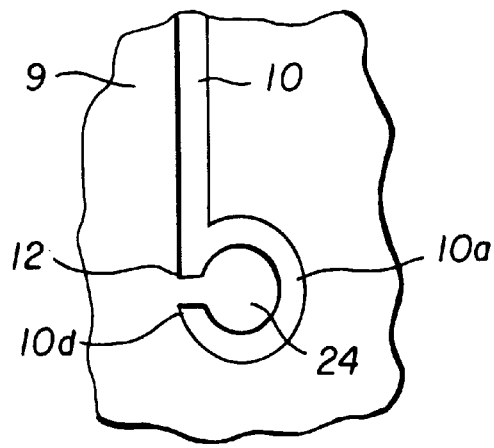

As shown in FIGS. 1 through 4, slot 10a is a simple transverse slot which intersects slot 10 at a right angle. While this is an effective arrangement, other configurations of slot 10a are possible. Three such arrangements are shown in FIGS. 9a through 9c. In FIG. 9a, slot 10a is configured as a T-shaped notch. This T-shaped notch comprises a first transverse leg 10b which intersects slot 10, and a second leg 10c which intersects the transverse leg and is substantially parallel to slot 10. If desired, transverse leg 10b and leg 10c may be configured as an L-shaped notch, as shown in FIG. 9b. The notches of FIGS. 9a and 9b operate in the following manner. Hub 2 is moved forward within the container until pin 7 reaches end 12 of slot 10. At this point, the needle is rotated by pushing pin 7 into transverse leg 10b of slot 10a until the pin reaches the point where legs 10b and 10c intersect. At this point, spring 16 biases the hub 2 away from ridge 15, causing pin 7 to enter leg 10c of slot 10a. Leg 10c acts as a stop, preventing spring 16 from decompressing further and causing needle 1 to retract into the container. Leg 10c also prevents the user from accidentally pushing pin 7 out of slot 10 a.

In FIG. 9c, slot 10a is configured as a C-shaped slot, where a first end of the C-shaped slot intersects slot 10 at point 12, and a second end 10d lies in line with slot 10. The end of slot 10 is separated from the second end of slot 10a by tab 24. The C-shaped configuration of slot 10a operates in the following manner. Hub 2 is moved forward within the container until pin 7 reaches end 12 of slot 10 At this point, the needle is rotated by pushing pin 7 along slot 10a until it reaches end 10d. At this point, spring 16 biases the hub 2 away from ridge 15, pressing pin 7 against tab 24. Tab 24 acts as a stop, preventing spring 16 from decompressing further and causing needle 1 to retract into the container.

Figure 5:
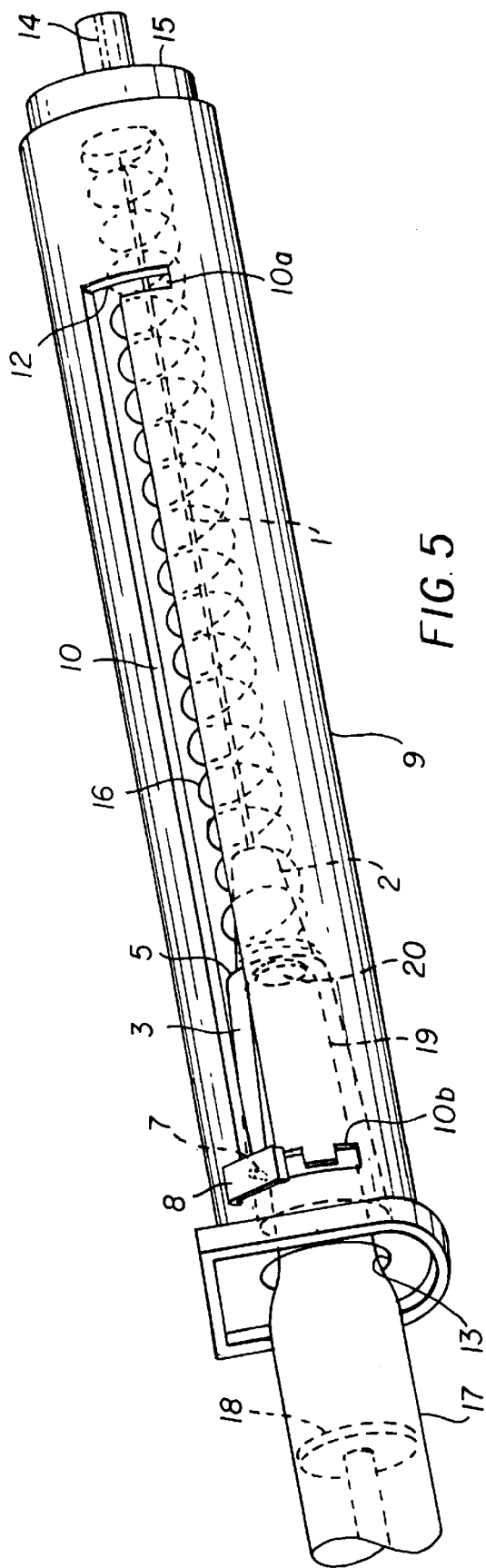
FIGS. 5 and 6 illustrate use of a syringe assembly with the safety needle of FIG. 3.
Figure 6:
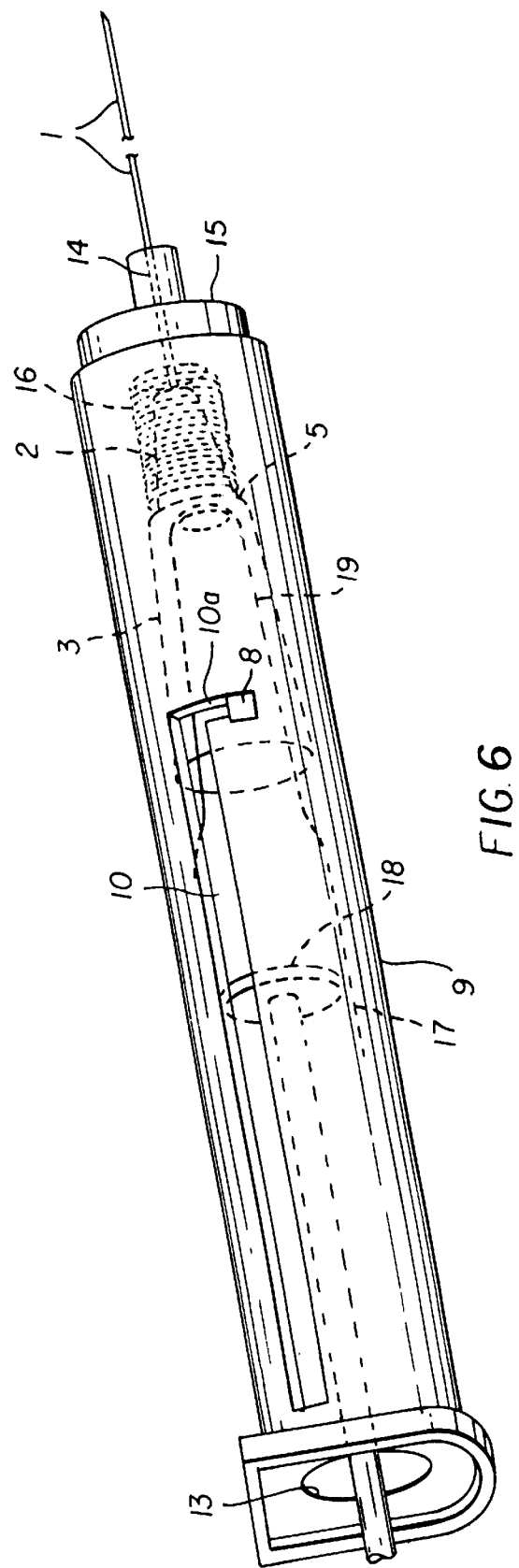

FIGS. 5 and 6 illustrate use of a syringe assembly with the safety needle of FIG. 3. The syringe comprises a syringe barrel 17, and a syringe plunger 18 slidably mounted therein. Barrel 17 has a frusto-conical tip 19 adapted to enter cavity 6 of sleeve 19 (cavity 6 is not shown in FIGS. 5 and 6, as it is occupied by tip 19.). Tip 19, after insertion into cavity 6, frictionally engages the interior of sleeve 3, forming a leakproof seal. A hole in tip 19 receives fluids which have passed through the bore of needle 1.

As shown in FIG. 6, syringe barrel 17 may be used to push the needle assembly within the container toward the second end of the container compressing the spring and causing needle 1 to emerge through hole 14. In this position, the container encases at least a portion of barrel 17. Barrel 17 may then be rotated causing sleeve 3 to rotate. This causes pin 7 to enter slot 10a, locking the syringe needle into position. The assembled syringe, with the needle exposed, may then be used So take a sample of a fluid. More particularly, the assembled syringe may be used to administer an injection to a patient, or to take a sample of arterial or venous blood from a patient.

After use, the contaminated needle may be discarded by rotating barrel 17 in the reverse direction to free pin 7 from slot 10a. This allows spring 16 to decompress, causing the container to slide forward of of the syringe barrel and cover needle 1. The syringe barrel may then be separated from sleeve 3, and the container with the needle concealed therein may be discarded with minimal risk of injury from contact with the contaminated needle. The syringe barrel and plunger may be discarded, or sterilized in an autoclave for reuse.

One difficulty in manufacturing an article of this type lies in the difficulty in getting the pin on the needle assembly to properly engage slot 10. For example, the invention of D'Amico (vide supra) presents a substantially cylindrical hub having a radially protruding pin attached thereto positioned within a tubular container. The inner circumference of the container is substantially the same as the outer circumference of the hub. The pin is positioned within a slot in the wall of the container, where each end of the slot is closed. However, this article is difficult to manufacture inexpensively. When the hub slides into the container, the radially protruding pin is blocked by the end of the tubular container wall, and cannot readily enter the container.

This invention attempts to solve this problem. When the container is manufactured in one piece, the combination of pin 7 and crosspiece 8 will not pass through slot 10 when the needle assembly of FIG. 1 is positioned inside the container of FIG. 2. To overcome this difficulty, one can position the needle assembly inside the container prior to attaching pin 7, and then insert pin 7 through slot 10 and secure the pin to sleeve 3.

Figure 7:
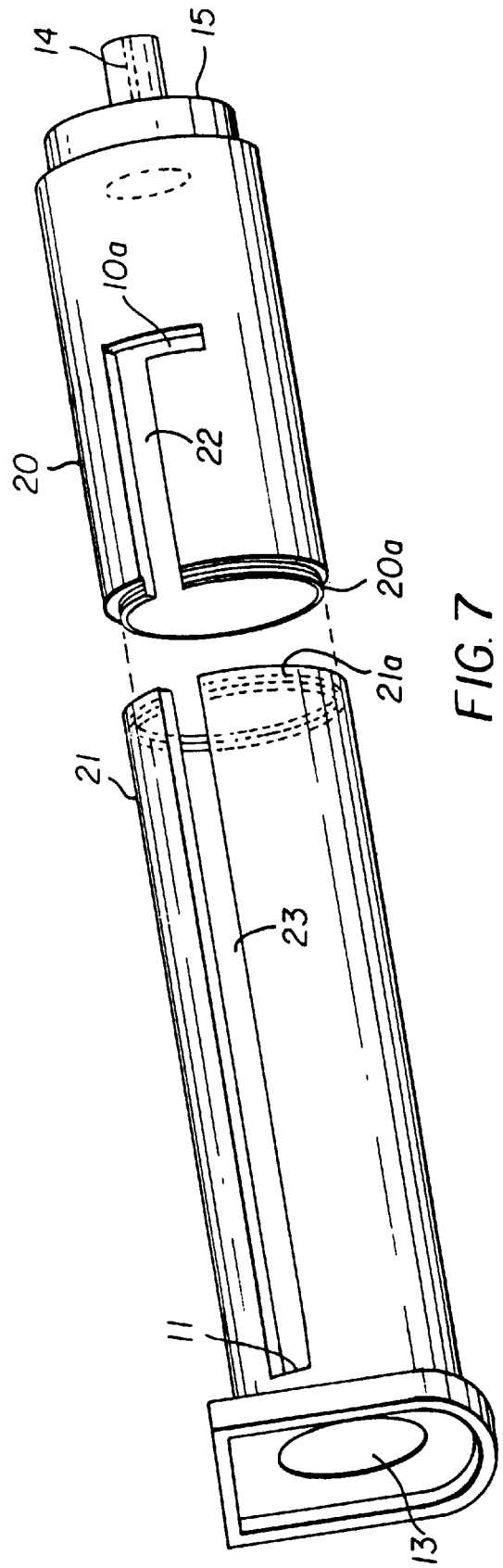
FIG. 7 illustrates the parts used to form the container of FIG. 2.

A second, and more preferred, method of solving the problem involves formation of the container in two parts, as shown in FIG. 7. The container is formed from an anterior portion 20 and a posterior portion 21. Anterior portion 20 has a first open end adapted to receive a syringe barrel and a second open end adapted to receive a hypodermic needle. Ridge 15 is positioned on the interior surface of the wall of anterior container portion 20. A first longitudinal slot 22 runs from the first end of the anterior portion of the container to point 12, near the second end of the anterior portion of the container. Slot 10a meets slot 22 at a right angle. Posterior portion 21 of the container has a first open end adapted to receive a syringe barrel and a second open end adapted to receive a syringe barrel. A second longitudinal slot 23 runs from the first end of the posterior portion of the container to point 11, near the second end of the posterior portion of the container. The first end of 20 and the first end of 21 are adapted to be joined together to form the complete container, by attaching 20 and 21 together so that slots 22 and 23 cooperate to form slot 10. The point of attachment between pieces 20 and 21 is shown in FIG. 2 as line 9a.

The manner in which 20 and 21 are joined together is not particularly limited. Parts 20 and 21 may be bonded together by means of a biocompatable adhesive. Alternatively, threaded ends on 20 and 21 may be screwed together, and then secured with a suitable adhesive. Also, a ridge on an interior surface of one piece may snap into a groove on an exterior surface of another piece. The ridge may be treated with an adhesive prior to snapping it into the groove. Finally, if 20 and 21 are made from a thermoplastic material (i.e., polyolefin), they may be heat-sealed together. In the embodiment illustrated in FIG. 8, a threaded end 20*a* on container portion 20 is screwed onto a threaded end 21*a* on container portion 21.

The complete assembly is manufactured in the following manner, shown in FIG. 8. A spring 16 and the needle assembly are joined together by joining a first end of the spring to ridge 5 on hub 2. The needle 1 is positioned along the helical axis of the spring. This assembly is then positioned within the anterior portion 20 of the container so that a second end of the spring engages ridge 15. Container portion 20 is then joined to container portion 21 so that:

a) slots 22 and 23 line up to form slot 10; and b) pin 7 is slidably engaged by slot 10.

Alternatively, hub 2 may be positioned within posterior portion 2 so that pin 7 engages slot 23, and then part 20 may be joined to part 21 container so that the second end of the spring engages ridge 15. Again, when joining pieces 20 and 21, care should be taken to ensure that slots 22 and 23 are aligned so as to form a single slot 10 which engages pin 7.

Figure 10:
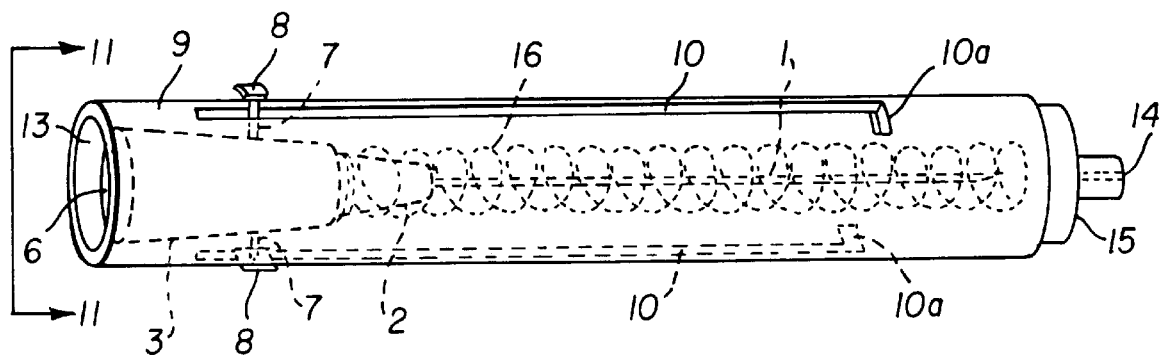
FIGS. 10 and 11 show a modified version of the apparatus of FIG. 3.
Figure 11:
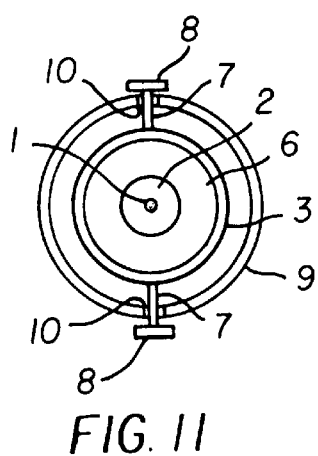

This assembly method allows the safety needle to be assembled quickly and easily, and avoids the difficulty of trying to position the needle inside a fully assembled container without damaging the pin by forcing it past the rim of the container As shown in FIG. 10, it is possible to secure two pins 7, each having a crosspiece 8 mounted thereto, on a single needle assembly, where the two pins are directed in opposite directions. Such a needle assembly may be mounted in a container having two slots 10*a* in opposite sides of wall 9. A transverse slot 10*a* intersects each slot 10, with each slot 10*a* running in the same direction (i.e., either clockwise or counterclockwise, when viewed from the second end of the container along the container axis). This version of the apparatus operates in the same manner as the assembled apparatus of FIG. 3. The only difference is that the presence of the second pin anchors hub 2 of the needle assembly more firmly along the axis of the container (FIG. 11).

The apparatus of FIG. 3 may also be used to administer fluids intravenously to a patient (FIG. 12). Needle 1 is exposed by sliding piece 8 forward toward needle-receiving opening 14, carrying hub 2 toward the second end of the container until the needle passes through opening 14 and is exposed. Piece 8 is then pushed sideways until pin 7 enters slot 10*a*, locking the needle into the exposed position. An IV bag 24 or other container for fluids to be administered intravenously is obtained. A first end of a tube 25 is connected to an opening 26 in the bag. The second end of the tube features a frusto-conical male joint 27. The second end of the tube 25 is secured to the syringe needle assembly. This is done by frictionally securing the male joint 27 to the inner surface of the frusto-conical cavity 6 defined by annular sleeve 3. Needle 1 is inserted into a patient's vein. Liquid contained in the IV bag is allowed to flow out of the bag, through the tube, and into the patient's vein. This is normally done by elevating the IV bag relative to the syringe needle assembly. The tube may also have a valve 28 or other mechanism for controlling the rate at which fluid from the IV bag enters the patient's arm. When needle 1 is withdrawn from the patient's vein, piece 8 is then pushed sideways until pin 7 exits slot 10*a*, unlocking the needle. Spring 16 then causes needle 1 to withdraw into the container.

FIG. 13 shows an alternative embodiment of the needle assembly of FIG. 1. This embodiment of the needle assembly features a hollow straight needle 29 having two ends. The needle 29 extends through a hub 30, so that a first end of the needle 29*a* points in a forward direction, and a second end of the needle 29*b* points in a reverse direction. Pin 7 is rigidly connected with said hub, and extends in a radial direction. Crosspiece 8 is connected with the pin at a defined distance from the hub. Preferably, a rubber sheath 31 covers end 29*b* of needle 1.

Figure 14:
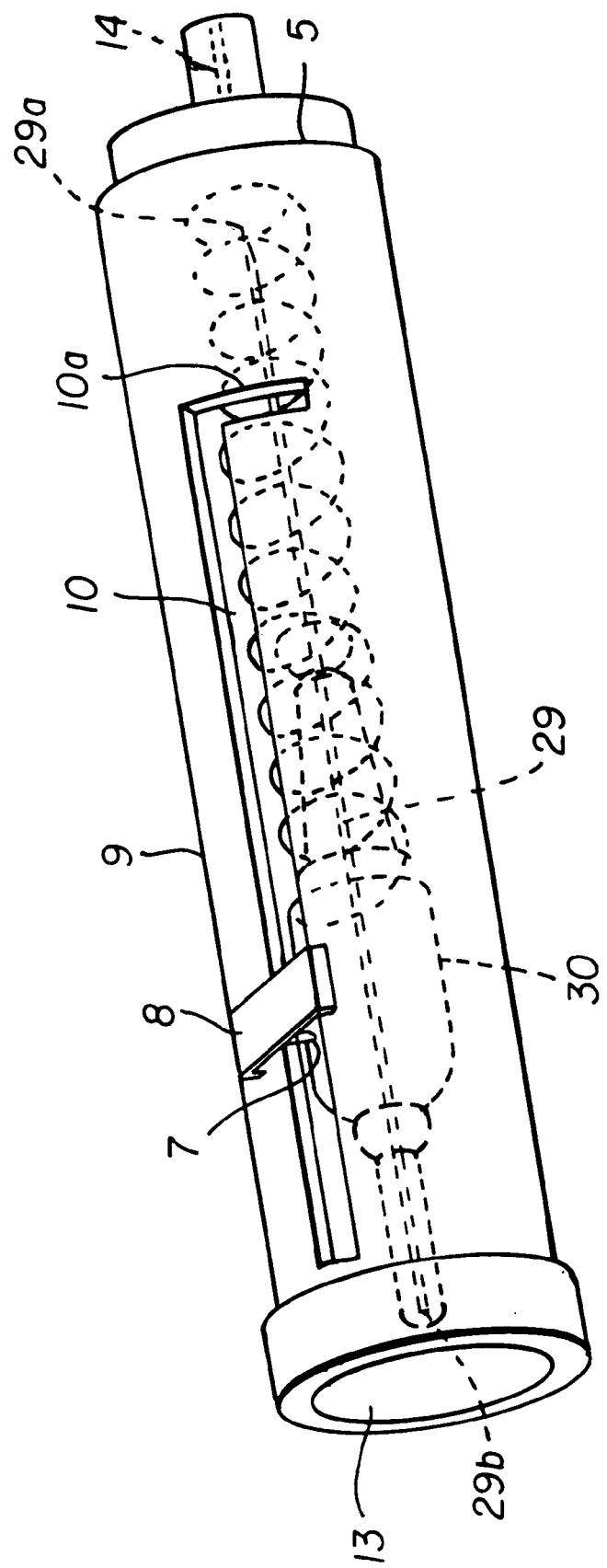
FIG. 14 shows an apparatus for taking blood samples, using the needle assembled of FIG. 13.

FIG. 14 shows the needle assembly of FIG. 13 mounted within the container of FIG. 2. Pin 7 is slidably engaged by the longitudinal slot 10, with crosspiece 8 acting to support hub 30 so that it is positioned on the axis of the container. Needle end 29*a* is directed toward needle-receiving opening 14. End 29*a* of needle 29 is exposed by using the thumb or finger to manually slide piece 8 forward toward needle-receiving opening 14, carrying hub 30 toward the second end of the container until the needle end 29*a* passes through opening 14 and is exposed. Piece 8 is then pushed sideways until pin 7 enters slot 10*a*, locking the needle into the exposed position. The needle may then be inserted into a patient's blood vessel. The rubber sheath prevents the patient's blood from traveling through the needle.

Figure 15:
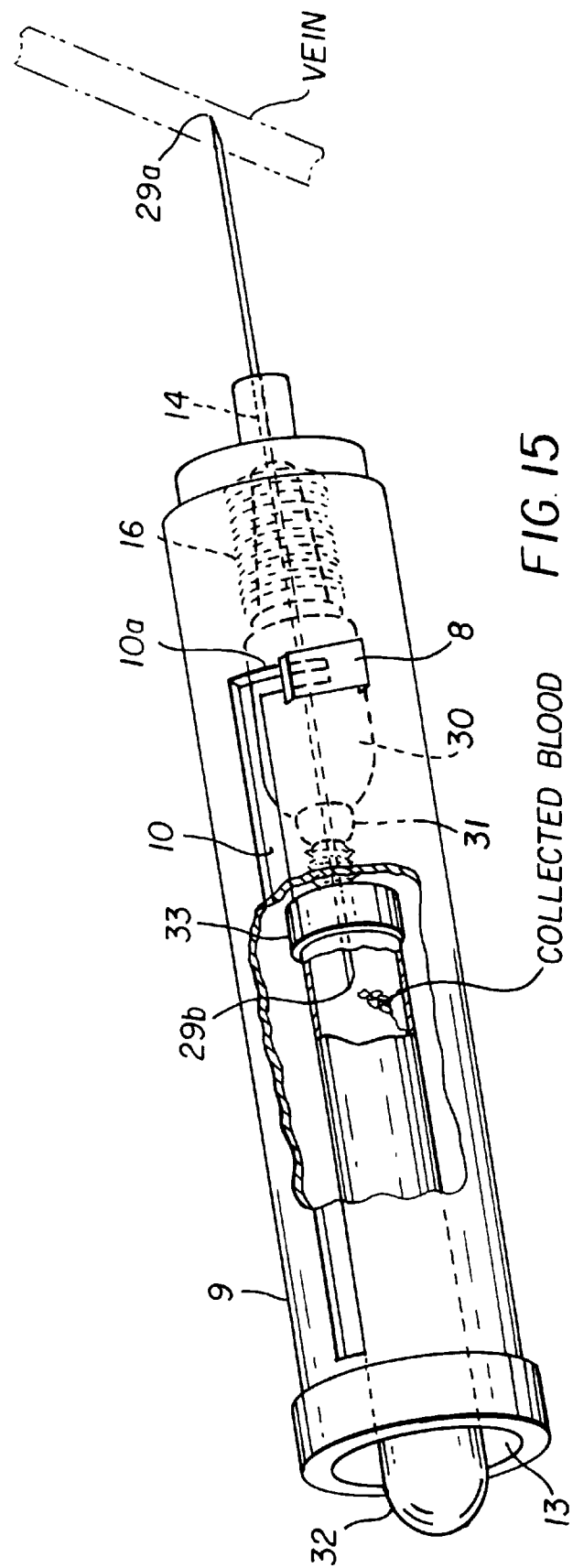
FIG. 15 shows the apparatus of FIG. 14 in use.

The assembly of FIG. 14 may be used with a receptacle for receiving a blood sample, as shown in FIG. 15. This receptacle is a test tube 32 having an open end. A rubber septum 33 seals the open end of the test tube. The interior of the test tube may be under vacuum. While needle 29 is in the patient's blood vessel, the end of the test tube which is sealed by septum 33 is inserted into opening 13 of the container until septum 33 contacts rubber sheath 31. The test tube is then pushed toward hub 30, and septum 33 pushes the end of rubber sheath 31 along needle 29 toward hub 30, exposing end 29*b* of needle 29. End 29*b* of needle 29 pierces the rubber sheath 31 and septum 33, entering the test tube. Blood from the patient then travels through hollow needle 29 into the test tube. After taking a sample of the patient's blood, test tube 32 is removed from the container. Rubber sheath 31 resumes its original configuration, covering end 29*b* of the needle and cutting off the flow of blood. Needle 29 is then withdrawn from the patient's blood vessel. Crosspiece 8 is then pushed sideways until pin 7 exits slot 10*a*, unlocking the needle. Spring 16 then causes needle 1 to withdraw into the container.

As in the syringe needle assembly of FIG. 3, piece 8 is sufficiently large that it cannot pass through slit 10 into the interior of the container, and is rigidly secured to a defined position along the length of pin 7, where the defined position on pin 7 is chosen so that hub 30 of the needle assembly is positioned along the cylindrical axis of the container. More particularly, the distance between the axis of hypodermic needle 1 and crosspiece 8 is equal to the one half the external diameter of the wall 9 of the container. This retains needle 29 along the axis of the container.

The use of crosspiece 8 to retain needle 1 in position is particularly important in an apparatus for obtaining blood samples. The container has to be wide enough to receive the test tube, which in turn is normally wider than hub 2. Without crosspiece 8, pin 7 would slip out of slot 10, and end 29*b* of needle 29 would fall against the inner surface of wall 9. Needle 29*b* would then be incorrectly positioned to penetrate septum 33. The needle assembly would also come out of the container.

Figure 16:
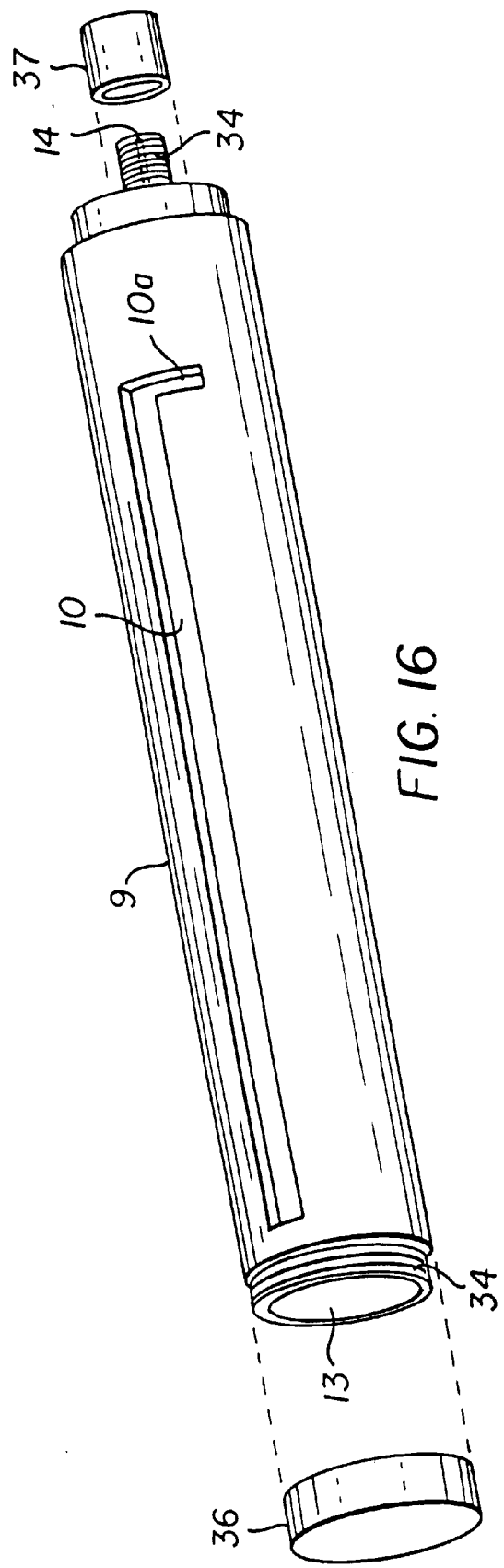
FIG. 16 shows the container of FIG. 2, having screw-on caps applied to each end.

As shown in FIG. 16 (note that the needle assembly has been omitted from FIG. 16 in the interests of clarity), a threaded male joint 34 may surround opening 13 at the first end of the container of FIG. 2, and a threaded male joint 35 may surround opening 14 at the second end of the container. Cap 36 having a threaded female joint may be screwed onto joint 34, covering opening 13, and cap 37 having a threaded female joint may be screwed onto joint 35, covering opening 14. This is normally done whenever the needle is not intended to be exposed, so as to minimize the risk of accidental contact with the tip of the needle.

What is claimed is:

1. A retractable syringe needle, comprising;
    a) a needle assembly featuring:
        a needle-holding mechanism, said needle-holding mechanism comprising a hub and an annular sleeve connected with said hub, said sleeve having an exterior surface and an interior surface, where said interior surface of said sleeve defines a frusto-conical cavity adapted to frictionally engage a frusto-conical fitting on a syringe barrel;
        a hypodermic needle extending through said hub; and
        a pin directly connected to the exterior surface of said annular sleeve;
    b) a container with a defined cylindrical axis having a tubular wall with a first longitudinal slot therein, said container having a first open end adapted to receive a syringe barrel and a second open end adapted to receive a syringe needle, said container having said needle assembly mounted therein so that the pin is slidably engaged by the first longitudinal slot, and so that said needle assembly may be moved from a first position where the needle is within the container to a second position where the needle is exposed by sliding the pin toward the second open end of the container and causing the needle to pass through the second open end;
    c) a means for biasing the needle assembly toward said first position; and
    d) a means for releasably engaging the pin at a defined location in said first longitudinal slot so as to hold said needle assembly in said second position;
    where the hub of said needle-holding mechanism is movably positioned along the defined cylindrical axis of the container, the position of the hub being maintained along the axis by a crosspiece rigidly fixed to a defined location along the length of the pin, said crosspiece being on the exterior of the container, and being unable to pass through the first longitudinal slot.

2. The retractable syringe needle of claim 1, wherein:
    said container is formed from:
        i) an anterior container portion having a tubular wall, said anterior portion of said container having a first open end adapted to receive a syringe barrel; a second open end adapted to receive a hypodermic needle; and a second longitudinal slot adapted to slidably engage said pin running from the first end of the anterior portion of the container to a defined point near the second end of the anterior portion of the container; and
        ii) a posterior container portion having a tubular wall, said posterior portion of said container having a first open end adapted to receive a syringe barrel and a second open end adapted to receive a syringe barrel, and a third longitudinal slot adapted to slidably engage said pin running from the first end of the posterior portion of the container to a defined point near the second end of the posterior portion of the container; where the anterior container portion and the posterior container portion are joined together to form the container so that the needle assembly is inside the container and so that the second and third longitudinal slits cooperate to form said first longitudinal slot which slidably engages said pin.

3. The retractable syringe needle of claim 1, wherein the biasing means is a spring.

4. The retractable syringe needle of claim 3, wherein the biasing means is a spring having a first end which is connected with the needle assembly and a second end which engages a ridge on the interior surface of the wall of the container.

5. The retractable syringe needle of claim 4, wherein said ridge is at said second open end of said container.

6. The retractable syringe needle of claim 1, wherein said means for releasably engaging the pin comprises a notch which intersects said first longitudinal slot at said defined location, so that said needle assembly may be releasably held in said second position by sliding said pin out of said longitudinal slit into said notch.

7. A retractable syringe needle, comprising;
    a) a needle assembly featuring:
        a needle-holding mechanism, containing a hub and a means for securing a syringe barrel to said hub;
        a hypodermic needle extending through said hub; and
        a pin connected with said hub;
    b) a container with a defined cylindrical axis having a tubular wall with a first longitudinal slot therein, said container having a first open end adapted to receive a syringe barrel and a second open end adapted to receive a syringe needle, said container having said needle assembly mounted therein so that the pin is slidably engaged by the first longitudinal slot, and so that said needle assembly may be moved from a first position where the needle is within the container to a second position where the needle is exposed by sliding the pin toward the second open end of the container and causing the needle to pass through the second open end;
    c) a means for biasing the needle assembly toward said first position; and
    d) a means for releasably engaging the pin at a defined location in said first longitudinal slot so as to hold said needle assembly in said second position;
    said container being formed from:
        i) an anterior container portion having a tubular wall, said anterior portion of said container having a first open end adapted to receive a syringe barrel; a second open end adapted to receive a hypodermic needle; and a second longitudinal slot adapted to slidably engage said pin running from the first end of the anterior portion of the container to a defined point near the second end of the anterior portion of the container; and
        ii) a posterior container portion having a tubular wall, said posterior portion of said container having a first open end adapted to receive a syringe barrel and a second open end adapted to receive a syringe barrel, and a third longitudinal slot adapted to slidably engage said pin running from the first end of the posterior portion of the container to a defined point near the second end of the posterior portion of the container;
            where the anterior container portion and the posterior container portion are joined together to form the container so that the needle assembly is inside the container and so that the second and third longitudinal slits cooperate to form said first longitudinal slot which slidably engages said pin.

8. The retractable syringe needle of claim 7, wherein the pin is connected to an external surface of said annular sleeve.

9. The retractable syringe needle of claim 7, wherein the biasing means is a spring.

10. The retractable syringe needle of claim 9, wherein the biasing means is a spring having a first end which is connected with the needle assembly and a second end which engages a ridge on the interior surface of the wall of the container.

11. The retractable syringe needle of claim 10, wherein said ridge is at said second open end of said container.

12. The retractable syringe needle of claim 1, wherein said means for releasably engaging the pin comprises a notch which intersects said first longitudinal slot at said defined location, so that said needle assembly may be releasably held in said second position by sliding said pin out of said longitudinal slit into said notch.

13. The retractable syringe needle of claim 7, wherein the needle assembly comprises:
a needle-holding mechanism, said needle-holding mechanism comprising a hub and an annular sleeve connected with said hub, said sleeve having an exterior surface and an interior surface, where said interior surface of said sleeve defines a frusto-conical cavity adapted to frictionally engage a frusto-conical fitting on a syringe barrel;
a hypodermic needle extending through said hub; and
a pin directly connected to the exterior surface of said annular sleeve.

14. A hypodermic syringe, comprising:
a) a needle assembly featuring:
a needle assembly featuring:
a needle-holding mechanism, said needle-holding mechanism comprising a hub and an annular sleeve connected with said hub, said sleeve having an exterior surface and an interior surface, where said interior surface of said sleeve defines a frusto-conical cavity;
a hypodermic needle extending through said hub; and
a pin directly connected to the exterior surface of said annular sleeve;
b) a hypodermic syringe barrel having a frusto-conical tip, said frusto-conical tip being frictionally and releasably engaged by the interior surface of the cavity in said sleeve;
c) a hypodermic syringe plunger slidably positioned inside the syringe barrel;
d) a container with a defined cylindrical axis having a tubular wall with a first longitudinal slot therein, said container having a first open end adapted to receive a syringe barrel and a second open end adapted to receive a syringe needle, said container having said needle assembly mounted therein so that the pin is slidably engaged by the first longitudinal slot, and so that said needle assembly may be moved from a first position where the needle is within the container to a second position where the needle is exposed by sliding the pin toward the second open end of the container and causing the needle to pass through the second open end;
e) a means for biasing the needle assembly toward said first position; and
f) a means for releasably engaging the pin at a defined location in said first longitudinal slot so as to hold said needle assembly in said second position;
where the hub of said needle-holding mechanism is movably positioned along the defined cylindrical axis of the container, the position of the hub being maintained along the axis of the container by a crosspiece rigidly fixed to a defined location along the length of the pin, said crosspiece being on the exterior of the container, and being unable to pass through the first longitudinal slot.

15. The hypodermic syringe of claim 14, wherein:
said container is formed from:
i) an anterior container portion having a tubular wall, said anterior portion of said container having a first open end adapted to receive a syringe barrel; a second open end adapted to receive a hypodermic needle; and a second longitudinal slot adapted to slidably engage said pin running from the first end of the anterior portion of the container to a defined point near the second end of the anterior portion of the container; and
ii) a posterior container portion having a tubular wall, said posterior portion of said container having a first open end adapted to receive a syringe barrel and a second open end adapted to receive a syringe barrel, and a third longitudinal slot adapted to slidably engage said pin running from the first end of the posterior portion of the container to a defined point near the second end of the posterior portion of the container; where the anterior container portion and the posterior container portion are joined together to form the container so that the needle assembly is inside the container and so that the second and third longitudinal slits cooperate to form said first longitudinal slot which slidably engages said pin.

16. The hypodermic syringe of claim 14, wherein the biasing means is a spring.

17. The hypodermic syringe of claim 16, wherein the biasing means is a spring having a first end which is connected with the needle assembly and a second end which engages a ridge on the interior surface of the wall of the container.

18. The hypodermic syringe of claim 17, wherein said ridge is at said second open end of said container.

19. The hypodermic syringe of claim 14, wherein said means for releasably engaging the pin comprises a notch which intersects said first longitudinal slot at said defined location, so that said needle assembly may be releasably held in said second position by sliding said pin out of said longitudinal slit into said notch.

20. The retractable syringe needle of claim 19, wherein the notch is a C-shaped slot.

21. A double-ended safety needle, comprising:
a) a needle assembly featuring a hub, a hollow straight needle, and a pin directly connected to said hub;
where the needle extends through the hub so as to expose a first end of the needle projecting in a first direction and a second end of the needle projecting in a second direction;
b) a container with a defined cylindrical axis having a tubular wall with a first longitudinal slot therein, said first longitudinal slot being closed at both ends, said container having a first open end adapted to receive a receptacle for venous blood and a second open end adapted to receive the hollow needle, said container having said needle assembly mounted therein so that (i) the first end of the needle is directed toward the second open end of the container, and (ii) the pin on the needle assembly is slidably engaged by the first longitudinal slot;

where said needle assembly may be moved from a first position where the needle is within the container to a second position where the first end of the needle is exposed by sliding the pin toward the second open end of the container and causing the first end of the needle to pass through the second open end;

c) a means for biasing the needle assembly toward said first position; and d) a means for releasably engaging the pin at a defined location in said first longitudinal slot so as to hold said needle assembly in said second position;

where the hub of said needle-holding mechanism is movably positioned along the defined cylindrical axis of the container, the position of the hub being maintained along the axis of the container by a crosspiece rigidly fixed to a defined location along the length of the pin, said crosspiece being on the exterior of the container, and being unable to pass through the first longitudinal slot; and where said container is formed from:

i) an anterior container portion having a tubular wall, said anterior portion of said container having a first open end adapted to receive a receptacle for venous blood; a second open end adapted to receive the first end of the needle; and an open-ended second longitudinal slot adapted to slidably engage said pin, said second longitudinal slot having an open end at the first end of the anterior portion of the container and a closed end at a defined point near the second end of the anterior portion of the container; and p3 ii) a posterior container portion adapted to slidably engage a receptacle for venous blood, said posterior portion of said container having a tubular wall, a first open end, and a second open end, where the anterior container portion and the posterior container portion are joined together to form the container so that the needle assembly is inside the container and so that the second longitudinal slot cooperates with the posterior container portion to form said first longitudinal slot which slidably engages said pin.

22. The double-ended safety needle of claim 21, wherein: said container is formed from:

i) an anterior container portion having a tubular wall, said anterior portion of said container having a first open end adapted to receive a receptacle for venous blood; a second open end adapted to receive the first end of the needle; and a second longitudinal slot adapted to slidably engage said pin, said second longitudinal slot running from the first end of the anterior portion of the container to a defined point near the second end of the anterior portion of the container; and ii) a posterior container portion adapted to slidably engage a receptacle for venous blood, said posterior portion of said container having a tubular wall, a first open end, a second open end, and a third longitudinal slot adapted to slidably engage said pin, said second longitudinal slot running from the first end of the posterior portion of the container to a defined point near the second end of the posterior portion of the container; where the anterior container portion and the posterior container portion are joined together to form the container so that the needle assembly is inside the container and so that the second and third longitudinal slits cooperate to form said first longitudinal slot which slidably engages said pin.

23. The double-ended safety needle of claim 21, wherein said receptacle for venous blood comprises a test tube having an open end, and a septum which seals the open end of the test tube, said test tube being adapted to be inserted through the first open end of the container with the open end of the test tube being directed toward the needle assembly until the second end of the needle penetrates the septum.

24. The double-ended safety needle of claim 21, additionally comprising an elastomeric sheath which covers the second end of the needle.

25. The double-ended safety needle of claim 21, wherein the biasing means is a spring.

26. The double-ended safety needle of claim 25, wherein the biasing means is a spring having a first end which is connected with the needle assembly and a second end which engages a ridge on the interior surface of the wall of the container.

27. The double-ended safety needle of claim 21, wherein said means for releasably engaging the pin comprises a notch which intersects said first longitudinal slot at said defined location, so that said needle assembly may be releasably held in said second position by sliding said pin out of said longitudinal slit into said notch.

28. A device for intravenous administration of fluids, comprising:

a) a container for a fluid to be administered intravenously;

b) a needle assembly comprising:
a needle assembly featuring:
a needle-holding mechanism, said needle-holding mechanism comprising a hub and an annular sleeve connected with said hub, said sleeve having an exterior surface and an interior surface, where said interior surface of said sleeve defines a frusto-conical cavity;
a hypodermic needle extending through said hub; and
a pin directly connected to the exterior surface of said annular sleeve;

c) a tube adapted to convey fluid from the container to the needle assembly, said tube having a first end which is connected with an opening in said container and a second end having a frusto-conical male joint which frictionally engages the interior surface of the sleeve, d) a sleeve with a defined cylindrical axis, said sleeve having a tubular wall with a first longitudinal slot therein, a first open end adapted to receive the second end of the tube for administering fluids intravenously, and a second open end adapted to receive the hypodermic needle, said sleeve having said needle assembly mounted therein so that the pin on the needle assembly is slidably engaged by the first longitudinal slot;

where said needle assembly may be moved from a first position where the needle is within the sleeve to a second position where the needle is exposed by sliding the pin toward the second open end of the sleeve and causing the first end of the needle to pass through the second open end;

e) a means for biasing the needle assembly toward said first position; and f) a means for releasably engaging the pin at a defined location in said first longitudinal slot so as to hold said needle assembly in said second position;

where the hub of said needle-holding mechanism is movably positioned along the defined cylindrical axis of the sleeve, the position of the hub being maintained along the axis of the sleeve by a crosspiece rigidly fixed to a defined location along the length of the pin, said crosspiece being on the exterior of the sleeve, and being unable to pass through the first longitudinal slot.

29. The device for intravenous administration of fluids of claim 28, wherein:

said sleeve is formed from:
  i) an anterior sleeve portion having a tubular wall, said anterior portion of said sleeve having a first open end adapted to receive a receptacle for venous blood; a second open end adapted to receive the first end of the needle; and a second longitudinal slot adapted to slidably engage said pin, said second longitudinal slot running from the first end of the anterior portion of the sleeve to a defined point near the second end of the anterior portion of the sleeve; and
  ii) a posterior sleeve portion adapted to slidably engage a receptacle for venous blood, said posterior portion of said sleeve having a tubular wall, a first open end, a second open end, and a third longitudinal slot adapted to slidably engage said pin, said second longitudinal slot running from the first end of the posterior portion of the sleeve to a defined point near the second end of the posterior portion of the sleeve; where the anterior sleeve portion and the posterior sleeve portion are joined together to form the sleeve so that the needle assembly is inside the sleeve and so that the second and third longitudinal slits cooperate to form said first longitudinal slot which slidably engages said pin.

30. The device for intravenous administration of fluids of claim 28, further comprising a means for controlling the rate at which fluid is conveyed from the container to the needle assembly.

31. The device for intravenous administration of fluids of claim 28, wherein the biasing means is a spring.

32. The device for intravenous administration of fluids of claim 31, wherein the biasing means is a spring having a first end which is connected with the needle assembly and a second end which engages a ridge on the interior surface of the wall of the sleeve.

33. The device for intravenous administration of fluids of claim 28, wherein said means for releasably engaging the pin comprises a notch which intersects said first longitudinal slot at said defined location, so that said needle assembly may be releasably held in said second position by sliding said pin out of said longitudinal slit into said notch.

* * * * *